(12) United States Patent
Kawajiri et al.

(10) Patent No.: US 9,534,262 B2
(45) Date of Patent: Jan. 3, 2017

(54) METHODS AND CONTROLLERS FOR SIMULATED MOVING BED CHROMATOGRAPHY FOR MULTICOMPONENT SEPARATION

(71) Applicant: Georgia Tech Research Corporation, Atlanta, GA (US)

(72) Inventors: Yoshiaki Kawajiri, Atlanta, GA (US); Matthew J. Realff, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 454 days.

(21) Appl. No.: 14/228,634

(22) Filed: Mar. 28, 2014

(65) Prior Publication Data

US 2014/0290645 A1    Oct. 2, 2014

Related U.S. Application Data

(60) Provisional application No. 61/806,016, filed on Mar. 28, 2013.

(51) Int. Cl.
| | |
|---|---|
| *C13B 20/14* | (2011.01) |
| *C13K 13/00* | (2006.01) |
| *C07H 1/08* | (2006.01) |
| *D21C 1/00* | (2006.01) |
| *B01D 15/18* | (2006.01) |

(52) U.S. Cl.
CPC ........... *C13B 20/14* (2013.01); *B01D 15/1821* (2013.01); *C07H 1/08* (2013.01); *C13K 13/007* (2013.01); *D21C 1/00* (2013.01)

(58) Field of Classification Search
CPC ......... C13B 20/14; C13K 13/007; C07H 1/08; D21C 1/00; B01D 15/1821
See application file for complete search history.

(56) References Cited

U.S. PATENT DOCUMENTS

| | | |
|---|---|---|
| 2,985,589 A | 5/1961 | Broughton et al. |
| 4,615,742 A | 10/1986 | Wright |
| 2007/0148750 A1 | 6/2007 | Hoshino et al. |

OTHER PUBLICATIONS

Hashimoto et al. "A New Process Combining Adsorption and Enzyme Reaction for Producing Higher-Fructose Syrup" *Biotechnology and Bioengineering* 25(10):2371-2393 (1983).
Mok et al. "Productive and Parasitic Pathways in Dilute Acid-Catalyzed Hydrolysis of Cellulose" *Industrial & Engineering Chemistry Research* 31(1):94-100 (1992).

*Primary Examiner* — David A Reifsnyder
(74) *Attorney, Agent, or Firm* — Myers Bigel, P.A.

(57) ABSTRACT

A system for reacting and separating solid and fluid components includes a series of sequential simulated moving bed (SMB) chromatography columns connected to form a circulation loop. Each SMB chromatography column includes an inlet and an outlet. A reactor is configured to receive a solid reactant and has an inlet and an outlet, and the reactor inlet is fluidly connected to an outlet of a first SMB chromatography column of the series of sequential SMB chromatography columns. The reactor outlet is fluidly connected to an inlet of a second SMB chromatography column of the series of sequential SMB chromatography columns.

22 Claims, 7 Drawing Sheets

Figure 7

METHODS AND CONTROLLERS FOR SIMULATED MOVING BED CHROMATOGRAPHY FOR MULTICOMPONENT SEPARATION

RELATED APPLICATIONS

This application claims priority to U.S. Provisional Application Ser. No. 61/806,016, filed Mar. 28, 2013, the disclosure of which is hereby incorporated by reference in its entirety.

FIELD OF THE INVENTION

The present invention relates to Simulated Moving Bed (SMB) chromatography, and more particularly, to SMB chromatography for multicomponent separation.

BACKGROUND

Figure 1:
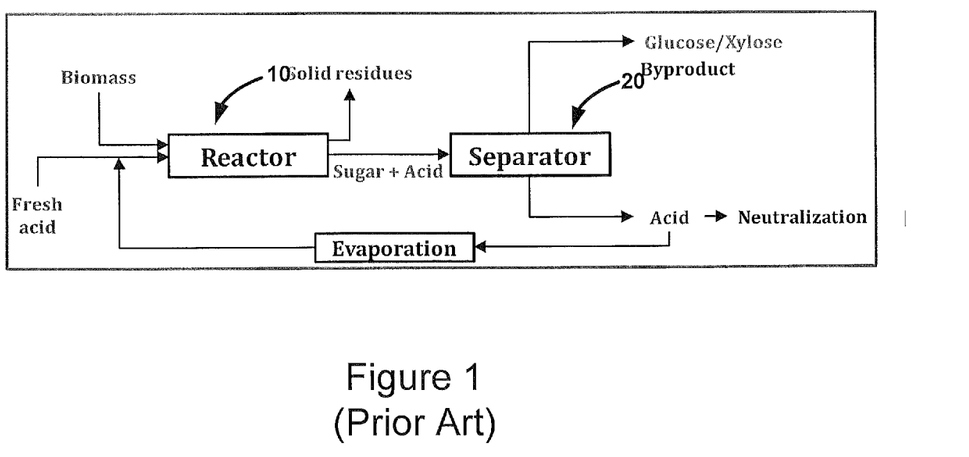
FIG. 1 is a schematic diagram of a prior art reactor, such as a Progressing Batch Hydrolysis (PBR) Reactor, for reacting a biomass and a Simulated Moving Bed (SMB) chromatography system for separating an acid and sugar.

Lignocellulosic biomass may be used as a feed stock for producing renewable fuels, such as ethanol. Lignocellulosic biomass generally includes cellulose (a primary sugar source for bioconversion processes), hemicelluloses (a secondary sugar source) and lignin, which includes phenylpropanoic acid moieties. Current processes for the conversion of lignocellulosic biomass to ethanol involve chemical and/or enzymatic treatment of the biomass to hydrolyze cellulose and hemicelluloses to their respective sugars. For example, as shown in FIG. 1, a biomass and an acid may be input into a reactor 10, such as a progressing batch hydrolysis reactor, which results in solid residues (e.g., cellulose and hemicelluloses) and a sugar/acid solution. In order to separate the sugar from the acid, a separator 20, such as a Simulated Moving Bed (SMB) chromatography separator is used. The glucose/xylose sugar byproducts may then be converted into ethanol using standard fermentation reactions.

Figure 2:
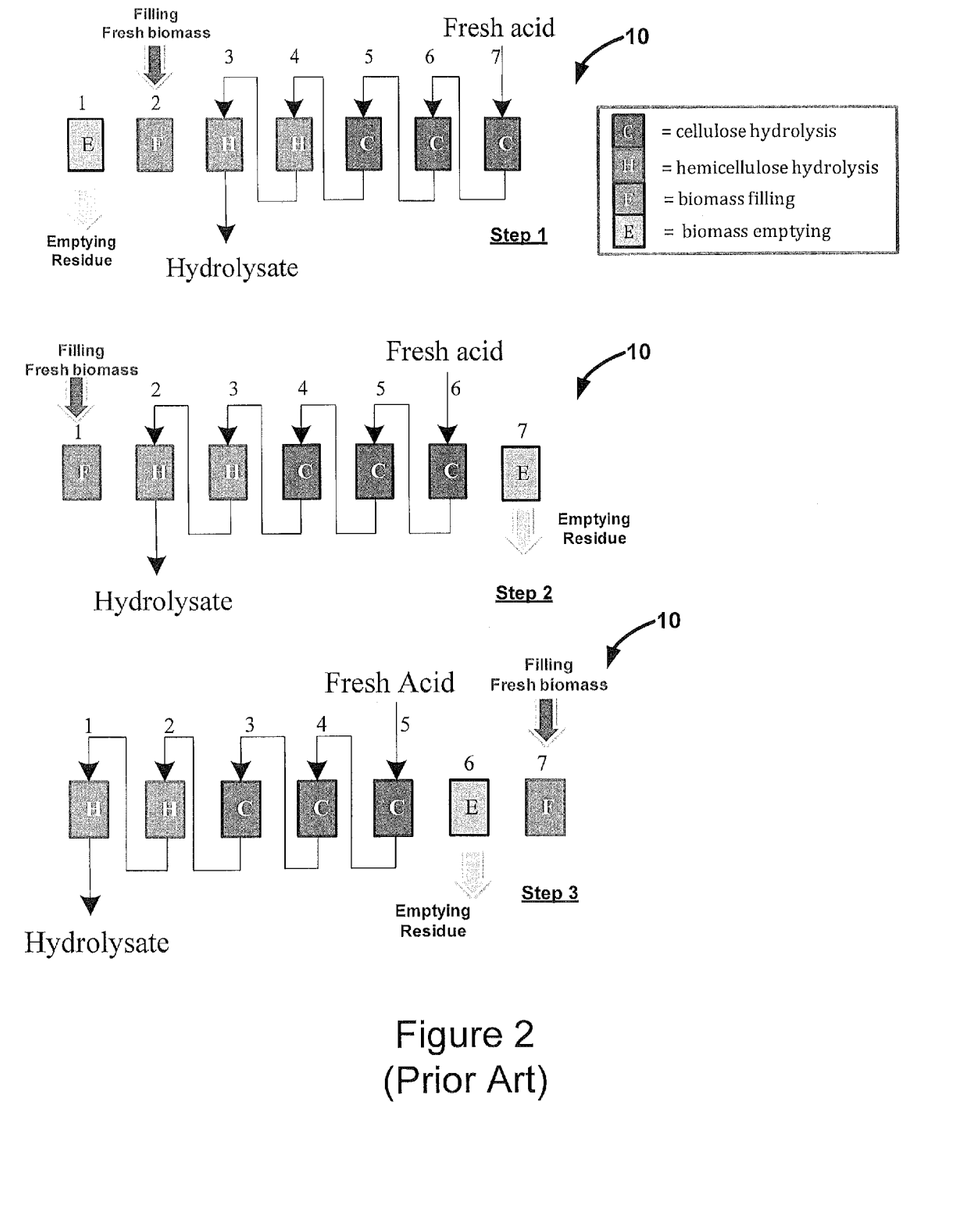
FIG. 2 is a schematic diagram of the PBR Reactor of FIG. 1.

An example of a progressing batch hydrolysis reactor 10 is shown in FIG. 2. As illustrated, seven reactors (1-7) are shown. In step 1, reactors 3-7 are interconnected so that acid is added to reactor 7 and flows sequentially to reactor 3, which outputs the hydrolysate, e.g., a sugar and acid solution. The unreacted or "fresh" biomass is added to reactor 2 and the residues of cellulose and hemicellulose is removed from reactor 1. In step 2, reactor 7 is suitable for emptying the cellulose and hemicelluloses, fresh biomass is filled in reactor 1, and reactors 2-6 are interconnected with reactor 6 receiving fresh acid input and reactor 2 outputting the hydrolysate sugar/acid solution. In step 3, reactor 6 is emptied of cellulose and hemicelluloses residue, reactor 7 is filled with biomass, and reactors 1-5 are interconnected with reactor 5 receiving fresh acid input and reactor 1 outputting the hydrolysate sugar/acid solution. The function of the reactors 1-7 may be rotated periodically in the sequence shown in steps 1-3. Accordingly, a series of hydrolysis reactors may be used to produce the sugar and acid solution from a biomass. Reactors indicated as hemicelluloses hydrolysis reactors typically operate at lower temperatures than the cellulose hydrolysis reactors to more efficiently process the biomass. Typical temperature ranges in such reactors are about 100° C.-220° C.

Figure 3:
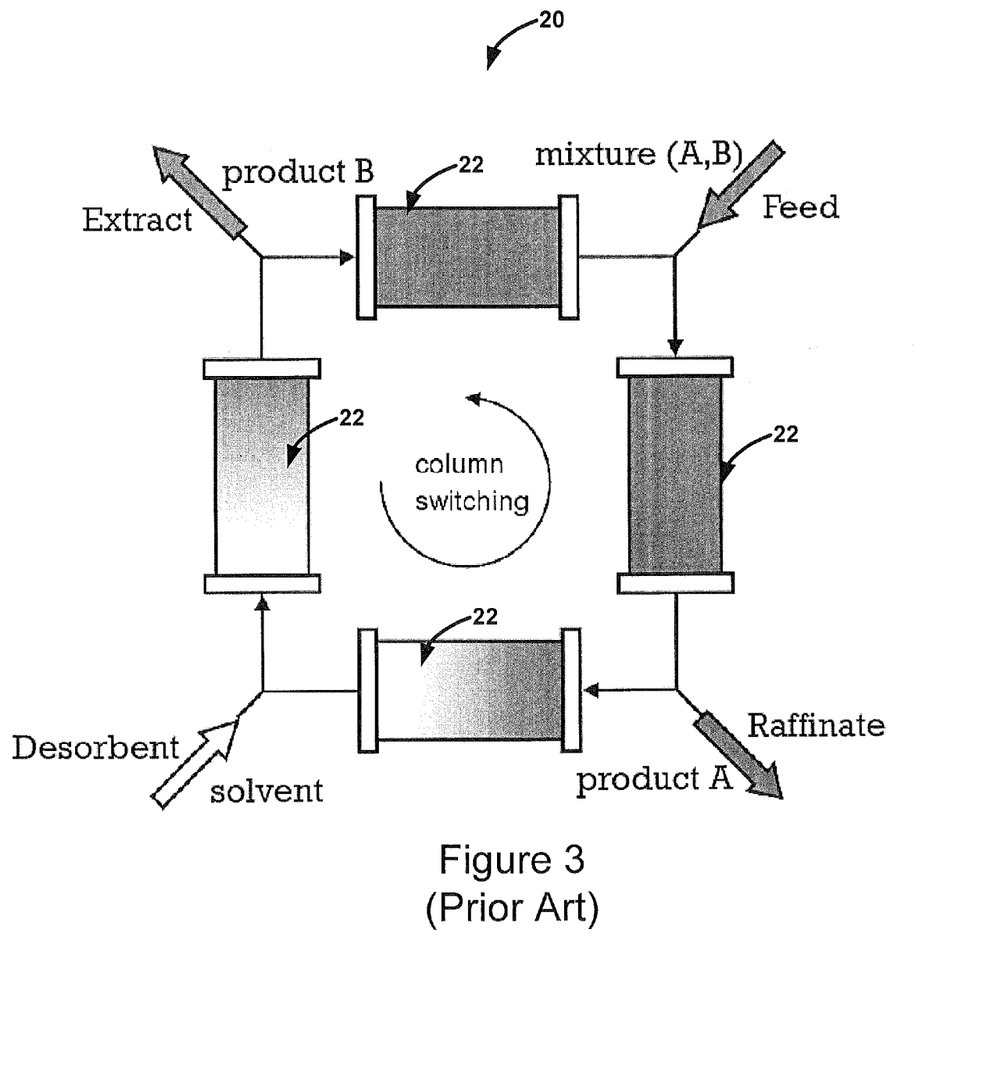
FIG. 3 is a schematic diagram of the SMB chromatography system of FIG. 1.

As shown in FIGS. 1-2, the resulting sugar/acid hydrolysate solution may be separated, for example, by using the hydrolysate as a feed input into simulated moving bed system 20 as shown in FIG. 3. The SMB process generally involves a flow scheme that takes advantage of continuous and counter-current movement of liquid and stationary phases without an actual movement of the solid. As shown in FIG. 3, a conventional SMB system 20 generally includes multiple chromatographic columns 22 that are interconnected in a cyclic formation. The feed and desorbent are supplied continuously, and at the same time, extract and raffinate streams are drawn continuously through the ports. The feed mixture includes two components that are separated due to their varying affinity towards the adsorbent phase in the columns. In the case of an acid and sugar feed mixture, the acid has a lower affinity and is the faster component compared to the sugar. The least retained component (acid) is recovered from the raffinate while the most retained component (sugar) is recovered through the extract stream outlet. The two inlet streams for the feed and desorbent and the two outlet streams for the extract and raffinate divide the SMB system 20 into four zones. This conventional SMB configuration with four zones has been extensively studied. As shown in FIG. 1, the acid output of the SMB separator may be neutralized or evaporated and recycled as fresh acid into the reactor of FIG. 2.

SUMMARY OF EMBODIMENTS OF THE INVENTION

In some embodiments, a system for reacting and separating solid and fluid components includes a series of sequential simulated moving bed (SMB) chromatography columns connected to form a circulation loop. Each SMB chromatography column includes an inlet and an outlet. A reactor is configured to receive a solid reactant and has an inlet and an outlet, and the reactor inlet is fluidly connected to an outlet of a first SMB chromatography column of the series of sequential SMB chromatography columns. The reactor outlet is fluidly connected to an inlet of a second SMB chromatography column of the series of sequential SMB chromatography columns.

In some embodiments, the reactor is a first reactor, and the system further includes a second reactor having an inlet and an outlet. The second reactor inlet is fluidly connected to an outlet of a third SMB column of the series of sequential SMB columns, and the second reactor outlet is fluidly connected to an inlet of a fourth SMB column of the series of sequential SMB columns. The first and/or second reactor may include two or more reactors connected in a series. The reactors may be hydrolysis reactors. The temperature of the first reactor may be different than the temperature of the second reactor. The first reactor may include a lignocellulosic biomass, and the first reactor may be configured to react cellulose from the biomass, and the second reactor may be configured to react hemicelluloses from the biomass. The series of sequential SMB chromatography columns may be configured to separate hemicellulosic sugars from biomass components of lignocellulosic biomass in the first and second reactors.

In some embodiments, a method for separating materials from a reaction includes positioning a solid material in a reactor. The reactor has an inlet and an outlet. A liquid is flowed through a series of sequential simulated moving bed (SMB) chromatography columns connected to form a circulation loop. Each SMB chromatography column includes an inlet and an outlet. The reactor inlet is fluidly connected to an outlet of a first SMB chromatography column of the series of sequential SMB chromatography columns, and the reactor outlet is fluidly connected to an inlet of a second SMB chromatography column of the series of sequential SMB chromatography columns so that the liquid flowing through the series of sequential SMB chromatographic columns comprises at least one reaction product from the reactor.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS OF THE INVENTION

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature, Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As used herein, the term "SMB" refers to simulated moving bed chromatography. SMB systems typically include a series of chromagraphic columns that are connected to form a loop. Each column may include an adsorbent with a particular affinity for a component in an SMB process.

As used herein, a "reactor" is a vessel for containing a reaction. Reactors may include an inlet for receiving the reactant or catalyst, which is typically an acid, and an outlet for outputting the liquid products of the reaction, which may include the reactant and any byproducts.

As used herein, a "feed mixture" or "feed" is a fluid (liquid or gas) that is introduced into a SMB system that includes various products that may be separated by the SMB system. Typically, a feed mixture includes components that are retained by various degrees by the adsorbent. The feed mixture may include any suitable components for separation, such as sugar, petrochemical and pharmaceutical separations.

As used herein, "raffinate" or "raffinate stream" is a product stream pumped from the SMB during operation that generally corresponds to the least retained component or components. The raffinate stream generally contains at least more than 50% by weight of the raffinate component(s), and may contain more than about 80%, 90%, 95% up to 99% or more by weight of the raffinate component(s).

As used herein, "extract" or "extract stream" is a product stream pumped from the SMB during operation that generally corresponds to the most retained component or components. The extract stream generally contains at least more than 50% by weight of the extract component(s), and may contain more than about 80%, 90%, 95% up to 99% or more by weight of the extract component(s).

As used herein, a "desorbent" is an eluent or mobile phase used to carry out the separation by moving a solute through a column in an SMB process. Examples of desorbents include water and methanol.

As used herein, an "adsorbent" is an adsorbing material in the SMB columns that has a particular affinity for a component in an SMB process. Typical adsorbents used in simulated moving bed adsorption processes generally include crystalline aluminosilicate zeolites and can comprise both the natural and synthetic aluminosilicates, silica gel or ion-exchange resins.

As used herein, the term "biomass" refers to, without limitation, organic materials produced by plants (such as leaves, roots, seeds and stalks), and microbial and animal metabolic wastes. Common biomass sources include: (1) agricultural residues, including corn stover, straw, seed hulls, sugarcane leavings, bagasse, nutshells, cotton gin trash, and manure from cattle, poultry, and hogs; (2) wood materials, including wood or bark, sawdust, timber slash, and mill scrap; (3) municipal solid waste, including recycled paper, waste paper and yard clippings; and (4) energy crops, including poplars, willows, switch grass, miscanthus, sorghum, alfalfa, prairie bluestream, corn, soybean, and the like. The term also refers to the primary building blocks of the above, namely, lignin, cellulose, hemicellulose and carbohydrates, such as saccharides, sugars and starches, among others.

In some embodiments, a chromatographic reactive separation process for solid reactants (e.g., a solid phase reactive separation system (SPRSS)) includes an integrated progressing batch reactor (PBR) and simulated moving bed (SMB) chromatographic separation system. In particular, one or more reactors may be positioned directly in the SMB loop. The reactors may be suitable for reacting a solid material, such as a biomass, and therefore, a solid material may be reacted and the resulting liquid reaction products may be separated in a single system.

Figure 4:
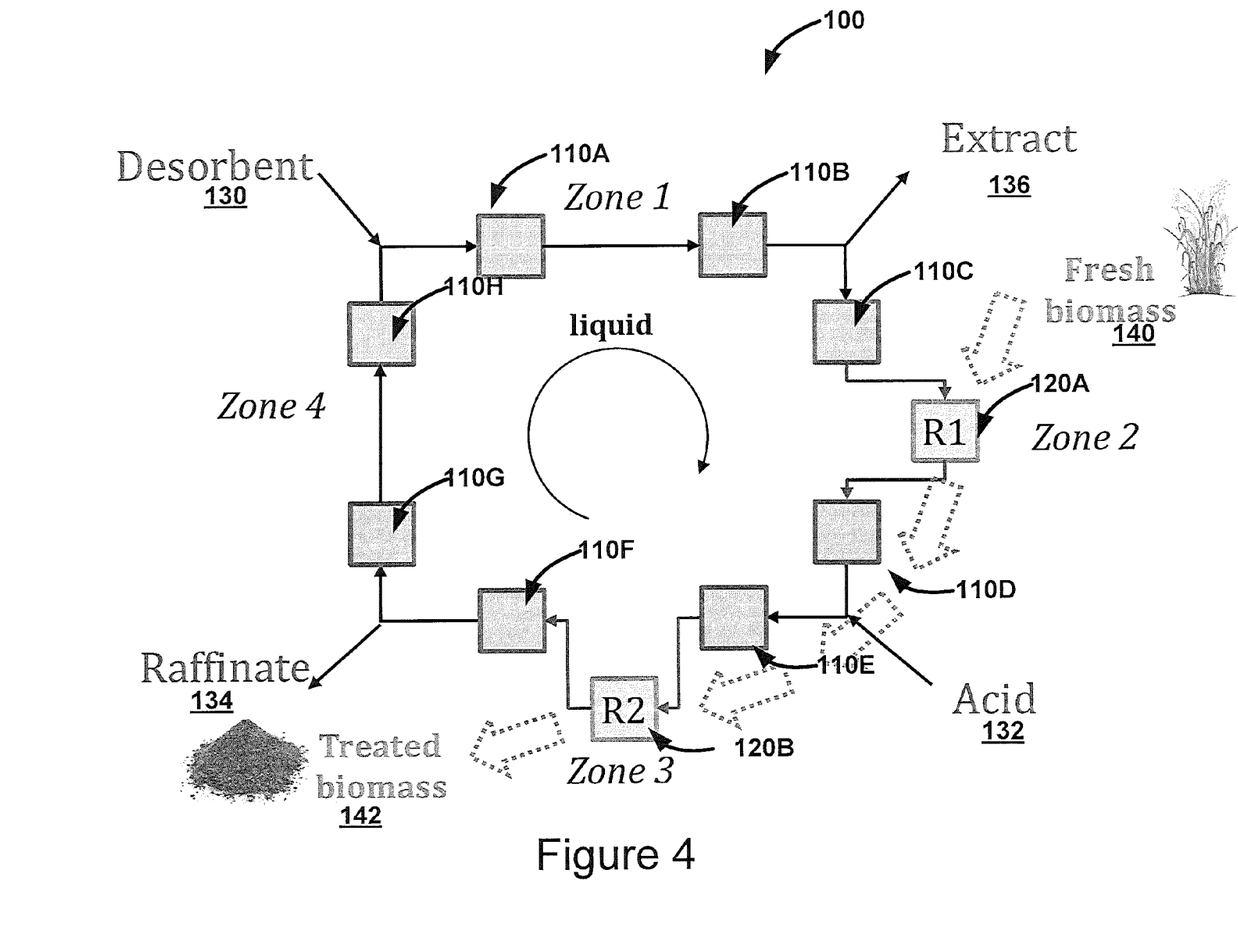
FIG. 4 is a schematic diagram of a Solid Phase Reactive Simulated Moving Bed Chromatographic Separation System according to some embodiments.

A solid phase reactive separation system 100 according to some embodiments is illustrated in FIG. 4. The system 100 includes a series of sequential SMB chromatographic columns 110A-110H and two reactors 120A, 120B. The reactors 120A, 120B are incorporated into the SMB chromatographic columns 110A-110H such that the output of one of the columns 110C is connected to an input to the reactor 120A, the output of the reactor 120A is connected to an input to the column 110D, the output of column 110E is connected to an input of the reactor 120B and the output of the reactor 120B is connected to an input of the column 110F. The columns 110A-110H have additional inputs for a desorbent 130 and an acid 132 and outputs for a raffinate 134 and an extract 136.

Examples of suitable SMB chromatographic columns are described in U.S. Pat. No. 2,985,589 and U.S. Patent Publication No. 2007/0148750, the disclosures of which are hereby incorporated by reference in their entireties. Examples of suitable hydrolysis reactors are described in U.S. Pat. No. 4,615,742 and in Mok, W. S.; Antal, M. J.; Varhegyi, G. Productive and parasitic pathways in dilute acid-catalyzed hydrolysis of cellulose. Industrial & Engineering Chemistry Research 1992. 31, 1, 94-100, the disclosures of which are hereby incorporated by reference in their entireties.

The system 100 of FIG. 4 may be used to separate hemicellulosic sugars from biomass components of lignocellulosic biomass as follows. A biomass 140 is positioned in the reactors 120A, 120B. A reactant or catalyst, such as an acid 132, is input into the reactor 120B via the column 110E to react with the biomass 140. A weaker acid is input into the reactor 120A from the column 110C as the acid 132 moves around the columns 110A-110H. The acid 132 may be any suitable acid, such as sulfuric acid, hydrochloric acid, or phosphoric acid. The acid 132 may also be in a concentration of about 0.5-50.0 wt %.

As illustrated in FIG. 4, the reactor 120A has a weaker acid concentration and may consequently react more hemicellulosic material in the biomass, and the reactor 120B has a stronger acid concentration, and may consequently react more cellulosic material in the biomass as compared with the reactor 120A. In some embodiments, the reactors 120A, 120B may be at different temperatures ranging from about 0 to 100° C., and at different pressures, for example, atmospheric pressure. In a typical biomass reaction, the reactor 120B would be at a higher temperature than the reactor 120A to facilitate reactions of the cellulose in the reactor 120B and reactions of the hemicellulose in the reactor 120A. Both reactors 120A, 120B output a hydrolysate that includes a sugar and the acid to the columns 110D and 110F, respectively. As shown, a raffinate 134, such as acid, is output between the columns 110F and 110G. A desorbent, such as water, is added to the system 100 between the columns 110H and 110A. An extract 136, such as hemicellolosic sugar, is output between the columns 110B and 110C.

Accordingly, a solid material, such as a biomass, may be reacted in one or more reactors 120A, 120B and the reaction outputs may be integrated into the SMB chromatographic columns 110A-110H so that the reaction outputs are separated by the columns 110A-110H in a single, interconnected system. Moreover, the acid raffinate 134 may be recycled and used as the acid 132 after an evaporation step.

In some embodiments, the reactors 120A, 120B, or the contents thereof, may be periodically switched and replenished. In particular, the reacted biomass from the reactor 120A may be situated in the position of the reactor 120B while the treated biomass 142 from reactor 120B is emptied. Fresh biomass 140 is then added to the reactor 120A. Accordingly, the reactor 120B may include biomass that has been previously treated in the reactor 120A to further facilitate the reaction of hemicellulose in the reactor 120A and cellulose in the reactor 120B. It should be understood that interchanging the contents of the reactors 120A, 120B may be accomplished by switching the input/output locations on physical reactors, physically moving the reactors, or moving the contents of the reactors.

Figure 5:
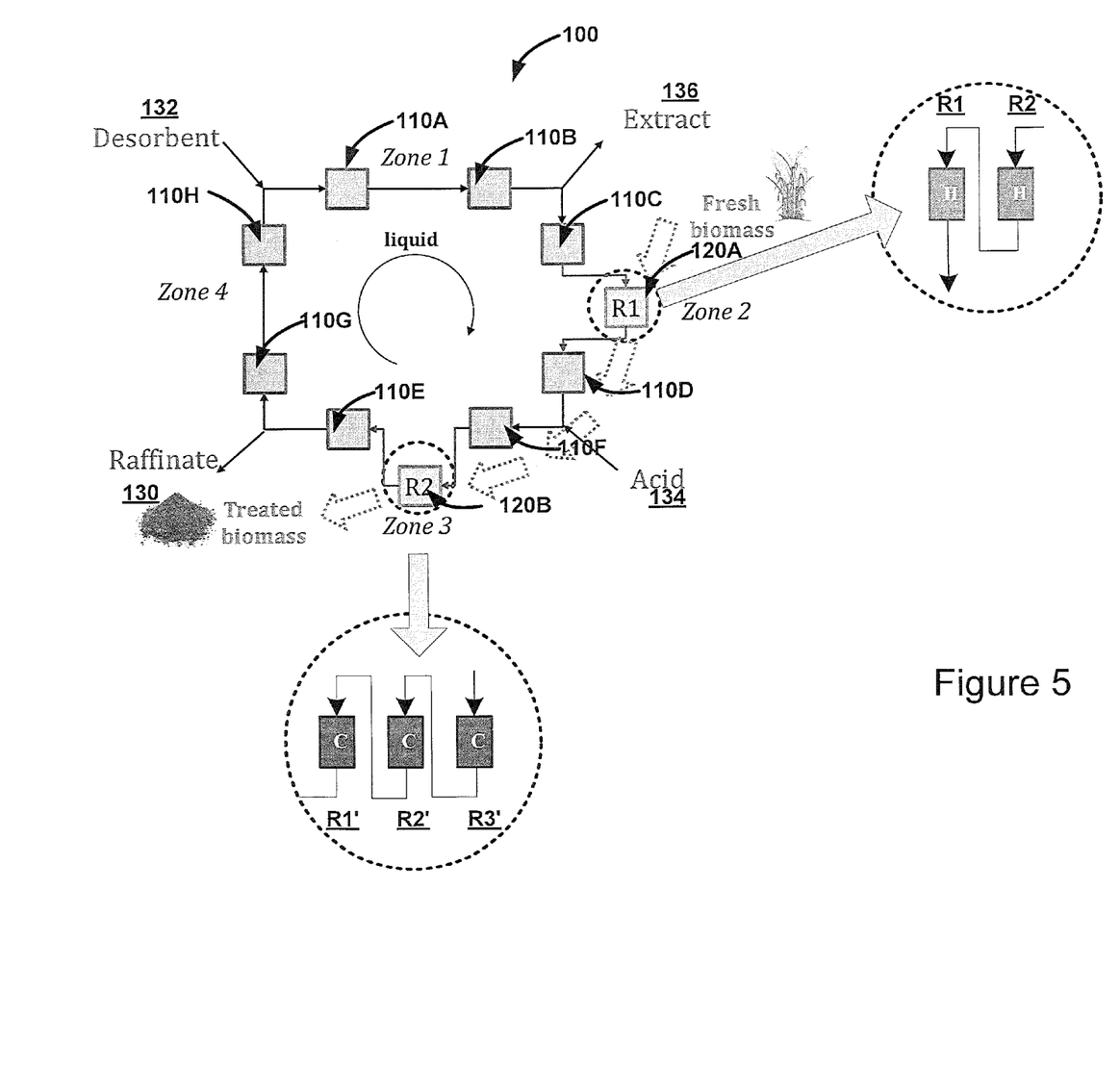
FIG. 5 is a schematic diagram of another Solid Phase Reactive Simulated Moving Bed Chromatographic Separation System according to some embodiments.

Although the reactors 120A, 120B are illustrated with respect to single reactors, it should be understood that any number or reactors or chromatographic columns may be used. For example, as illustrated in FIG. 5, the reactor 120A may include two reactors R1, R2 that are configured for reacting hemicelluloses, and the reactor 120B may include three reactors R1', R2', R3' that are configured for reacting cellulose. The reactors R1, R2 and R1', R2', R3' may be operated under different conditions, such as temperature and acidity level, based on the desired reaction. For example, the reactors R1, R2 and R1', R2', R3' be used at the same or different temperatures and have different acid and/or biomass compositions to facilitate reactions of the cellulose or hemicellulose. The reactors R1, R2 and R1', R2', R3' may be sequentially emptied and filled with fresh solid materials periodically.

Figure 6:
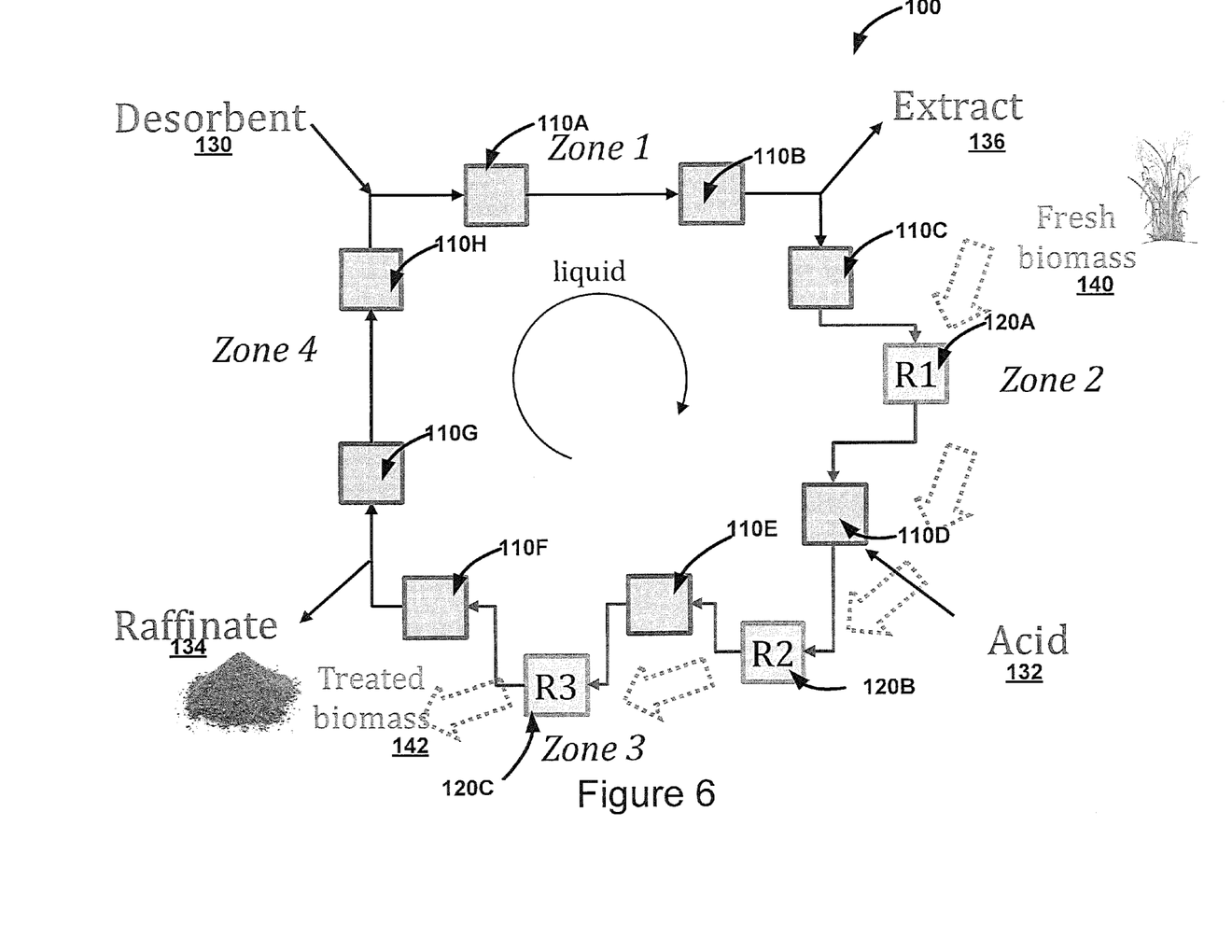
FIG. 6 is a schematic diagram of another Solid Phase Reactive Simulated Moving Bed Chromatographic Separation System according to some embodiments.
Figure 7:
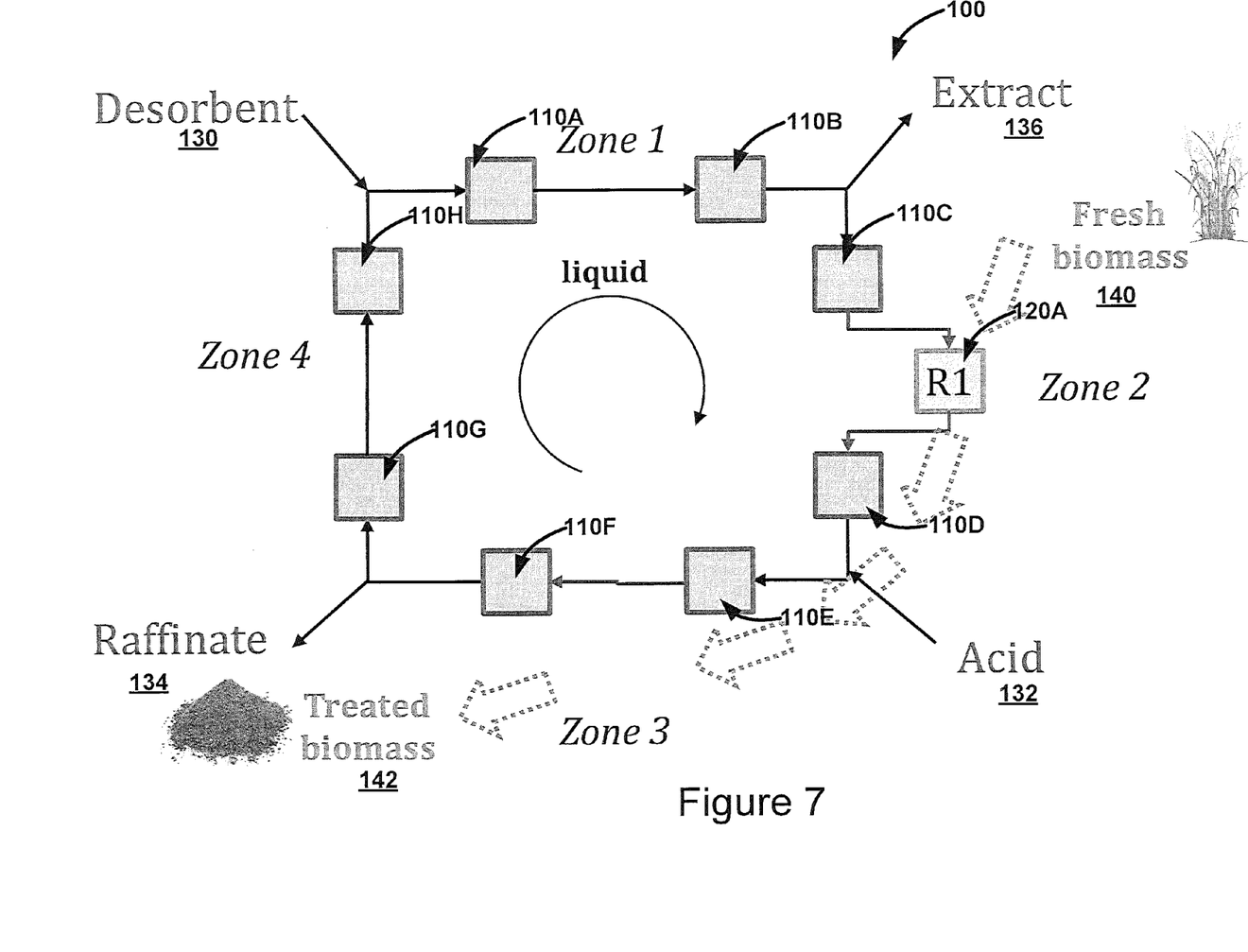
FIG. 7 is a schematic diagram of another Solid Phase Reactive Simulated Moving Bed Chromatographic Separation System according to some embodiments.

Although embodiments according to the invention are illustrated with respect to the reactors 120A, 120B and columns 110A-110H, it should be understood that any suitable configuration of reactors and columns may be used. For example, FIG. 6 illustrates a system 100 with three reactors 120A-120C integrated within the SMB chromatographic columns 110A-110H. FIG. 7 illustrates a system 100 with a single reactor 120A integrated within the SMB chromatographic columns 110A-110H.

Although the system 100 may be suitable for separating hemicellulosic sugars from biomass components of a lignocellulosic biomass, other reactions and separations may be performed in the system 100. For example, the system 100 may be used for the hydrolysis leaching of minerals from soil or clay, protein decomposition, or depolymerization reactions.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A system for reacting and separating solid and fluid components, the system comprising:
    a series of sequential simulated moving bed (SMB) chromatography columns connected to form a circulation loop, each SMB chromatography column comprising an inlet and an outlet; and
    a reactor configured to receive a solid reactant, the reactor having an inlet and an outlet, wherein the reactor inlet is fluidly connected to an outlet of a first SMB chromatography column of the series of sequential SMB chromatography columns, and the reactor outlet is fluidly connected to an inlet of a second SMB chromatography column of the series of sequential SMB chromatography columns.

2. The system of claim 1, wherein the reactor comprises a first reactor, and the system further comprises a second reactor having an inlet and an outlet, wherein the second reactor inlet is fluidly connected to an outlet of a third SMB column of the series of sequential SMB columns, and the second reactor outlet is fluidly connected to an inlet of a fourth SMB column of the series of sequential SMB columns.

3. The system of claim 2, wherein the first reactor comprises two or more reactors connected in a series.

4. The system of claim 3, wherein the second reactor comprises two or more reactors connected in a series.

5. The system of claim 2, wherein the first reactor and the second reactor are hydrolysis reactors.

6. The system of claim 5, wherein a temperature of the first reactor is different than a temperature of the second reactor.

7. The system of claim 2, further comprising a lignocellulosic biomass in the first reactor.

8. The system of claim 7, wherein the first reactor is configured to react cellulose from a lignocellulosic biomass.

9. The system of claim 8, wherein the second reactor is configured to react hemicelluloses from a lignocellulosic biomass.

10. The system of claim 9, wherein the series of sequential SMB chromatography columns are configured to separate hemicellulosic sugars from biomass components of lignocellulosic biomass in the first and second reactors.

11. The system of claim 1, wherein the reactor comprises two or more reactors connected in a series.

12. A method for separating materials from a reaction, the method comprising:
    positioning a solid material in a reactor; the reactor having an inlet and an outlet; and
    flowing a liquid through a series of sequential simulated moving bed (SMB) chromatography columns connected to form a circulation loop, each SMB chromatography column comprising an inlet and an outlet, wherein the reactor inlet is fluidly connected to an outlet of a first SMB chromatography column of the series of sequential SMB chromatography columns, and the reactor outlet is fluidly connected to an inlet of a second SMB chromatography column of the series of sequential SMB chromatography columns so that the liquid flowing through the series of sequential SMB chromatographic columns comprises at least one reaction product from the reactor.

13. The method of claim 12, wherein the reactor comprises a first reactor, and a second reactor having an inlet and an outlet is fluidly connected to the series of SMB chromatographic columns so that the second reactor inlet is fluidly connected to an outlet of a third SMB column of the series of sequential SMB columns, and the second reactor outlet is fluidly connected to an inlet of a fourth SMB column of the series of sequential SMB columns.

14. The method of claim 13, wherein the first reactor comprises two or more reactors connected in a series.

15. The method of claim 13, wherein the second reactor comprises two or more reactors connected in a series.

16. The method of claim 13, wherein the first reactor and the second reactor are hydrolysis reactors.

17. The method of claim 16, wherein a temperature of the first reactor is different than a temperature of the second reactor.

18. The method of claim 13, wherein the solid material comprises a lignocellulosic biomass.

19. The method of claim 18, further comprising maintaining the first reactor under conditions sufficient to react cellulose from a lignocellulosic biomass.

20. The method of claim 19, further comprising maintaining the second reactor under conditions sufficient to react hemicelluloses from a lignocellulosic biomass.

21. The method of claim 20, further comprising separating hemicellulosic sugars from biomass components of lignocellulosic biomass in the first and second reactors and further separating hemicellulosic sugars from acid in the series of sequential SMB chromatography columns.

22. The method of claim 12, wherein the reactor comprises two or more reactors connected in a series.

* * * * *